United States Patent [19]

Byrum

[11] Plant 4,407

[45] Apr. 17, 1979

[54] YELLOW ROSE SEEDLING (SEEDLING #71-57Y)

[75] Inventor: Roy L. Byrum, Richmond, Ind.

[73] Assignee: Joseph H. Hill Company, Richmond, Ind.

[21] Appl. No.: 885,697

[22] Filed: Mar. 13, 1978

[51] Int. Cl.[2] ..... A01H 5/00

[52] U.S. Cl. ..... Plt./24

[58] Field of Search ..... Plt./15, 24

*Primary Examiner*—Robert E. Bagwill

*Attorney, Agent, or Firm*—Chas. W. Rummler

[57] ABSTRACT

A new variety of yellow floribunda rose plant distinguished by the deep rich color of its blooms and the high glossy green color of its foliage which enhances the beauty of the flower; by the improved vase life performance of the cut flowers for holding color and shape; by its vigorous growing habit and resistance to disease; and by its free and continuous blooming habit under greenhouse culture.

10 Drawing Figures

BACKGROUND OF THE NEW PLANT

This new variety of yellow rose plant originated as a seedling resulting from breeding efforts carried on by me at Richmond, Ind., with the object of producing rose plants having better flower production and growing habits as well as improved color and keeping qualities. The crossing to produce this plant was done in March 1970 and the first flower from the resulting seedling occurred in October 1971. The improved and favorable characteristics of the new plant led to my asexual propagation of the plant by budding at Richmond, Ind., and further propagation under my direction through successive generations at Hamilton City, Calif., has demonstrated that its distinctive features hold true from generation to generation and appear to be firmly fixed. Greenhouse propagation and growing of this new plant in preparation for introduction to the commercial market has been carried on at Richmond, Ind., since 1973.

DESCRIPTION OF THE DRAWING

My new variety of yellow rose plant is illustrated by the accompanying photographic drawing which shows, in full color, newly opened and three-day opened flowers, several stages of bud opening, young and mature leaves, and specimens of young and old wood, the colors shown being as nearly true as can be obtained by conventional photographic procedures.

DESCRIPTION OF THE NEW PLANT

The following is a detailed description of my new rose plant with designations of color according to Koster's Color Guide (K) and the Horticultural Colour Chart (HCC) published by The Royal Horticultural Society of London, England, with collaboration of the British Colour Council, the data herein being derived from observations made in December 1977 of greenhouse plants grown at Richmond, Ind.

THE PLANT

Origin: Seedling.

Parentage:

*Seed parent.*—Spanish Sun, P.P. 2,809.

*Pollen parent.*—Hoosier Gold, P.P. 3,544.

Classification:

*Botanic.*—Hybrida.

*Commercial.*—Floribunda.

Form: Bush.

Habit: Upright and branched.

Growth: Free and vigorous with strong canes of medium diameter.

Main stems: Color — Cedar Green, (K) Plate #80, some stems with blotches of Maroon, (K) Plate #97.

*Thorns.*—Several, of medium length with a slight downward hook and with a short narrow base.

*Color.*—Mahogany, (K) Plate #95.

Branches: Color — Scheeles Green, (HCC) 860.

*Thorns.*—Several, of medium length and slightly hooked downward from a short narrow base.

*Color.*—Deep Purple, (K) Plate #52.

New shoots: Color — Scheeles Green, (HCC) 860/3, overlaid with Spinel Red, (HCC) 0023/2, to Spinel Red, 0023/3.

*Thorns.*—Several, of medium length and slightly hooked downward from a short narrow base.

*Color.*—Spinel Red, (HCC) 0023.

Foliage: Quantity — of normal abundance and of medium large size.

*Leaves.*—Shape — odd pinnate, with 3 to 5 leaflets.

*Shape of leaflets.*—Ovoid with obtuse base, acute apex and simply serrate margins.

*Aspect.*—Moderately heavy glossy.

*Color.*—Mature Leaf: Upper Surface — Nearest — Spinach Green, (HCC) 0960. Under Surface — Nearest — Apple Green, (K) Plate #77. Young Leaf: Upper Surface — Scheeles Green, (HCC) 860/3, overlaid with Deep Carmine Violet, (K) Plate #46, mostly at edge of leaf. Under Surface — Nearest — Deep Carmine Violet, (K) Plate #46.

*Rachis.*—Medium heavy, grooved on upper side and sparsely prickly on under side.

*Stipules.*—Short and very narrow with points which are very short and turning out at an angle of 90°.

THE BUD

Before calyx breaks:

*Size.*—Medium small.

*Form.*—Ovoid and short pointed with a conspicuous neck and foliaceous appendages which extend beyond the bud for a distance equal to about one-quarter of the bud length.

*Color of calyx.*—Scheeles Green, (HCC) 860/3.

As calyx breaks:

*Color, outside of petals.*—Chrome Yellow, (HCC) 605.

As first petal opens:

*Bud size.*—Medium small.

*Form.*—Ovoid.

*Color of petal.*—Outside: Chrome Yellow, (HCC) 605. Inside: Indian Yellow, (HCC) 6/1.

Bud opening: Very well in greenhouse.

Sepals: Permanent, of medium length, and spear-shaped.

*Color.*—Inside: Scheeles Green, (HCC) 860/2, overlaid with white fuzz. Outside: Scheeles Green, (HCC) 860/2, with streaks of Van Dyke Brown, (K) Plate #96.

Peduncle: Long, strong and erect, and of medium diameter.

Bark: Entirely smooth.

*Color.*—Scheeles Green, (HCC) 860/1. (Some of Scheeles Green, 860/2.)

*Thorns, prickles and hairs.*—None.

THE FLOWER

Blooming habit: Free and continuous in greenhouse.

Borne: Singly, on strong disbudded stems of medium length.

Size of bloom: Medium large, 2½ to 3 inches in diameter when fully opened.

Form: Full and high centered at first, with petals very tightly rolled outward, becoming open with petals loosely rolled outward upon maturity.

Petalage: Double with 25 to 30 petals regularly arranged.

*Shape.*—Outside Petals: Obovate, with obtuse apex. Intermediate Petals: Obovate, with obtuse apex. Inside Petals: Obovate, with obtuse apex, some with a notch.

*Texture.*—Moderately thick.

*Aspect.*—Inside: Satiny; Outside: Shiny.

Color of petals:

A. The following observations were made of a newly opened flower in greenhouse at Richmond, Ind., in December of 1977.

*Outside petals.*—Outer Surface: Chrome Yellow, (HCC) 605, at base, gradually changing to 605/1 at top. Inside Surface: Chrome Yellow, (HCC) 605, at base, gradually changing through 605/1 to 605/2 at top of petal.

*Intermediate petals.*—Outer Surface: Chrome Yellow, (HCC) 605, at base, changing to 605/1 toward top of petal. Inside Surface: Chrome Yellow, (HCC) 605, at base, gradually changing to 605/1 at top of petal.

*Inner petals.*—Outer Surface: Chrome Yellow, (HCC) 605/1. Inside Surface: Chrome Yellow, (HCC) 605.

B. The following observations were made of a greenhouse flower opened for 3 days in December 1977 at Richmond, Ind.

*Outside petals.*—Outer Surface: Empire Yellow, (HCC) 603/1, at base, gradually changing through 603/2 to 603/3 at top. Inside Surface: Empire Yellow, (HCC) 603, at base, gradually changing through 603/1, to 603/2 to 603/3 at top.

*Intermediate petals.*—Outer Surface: Empire Yellow, (HCC) 603/1, at base, gradually changing through 603/2, to 603/3 at top. Inside Surface: Empire Yellow, (HCC) 603, at base, gradually changing through 603/2, to 603/3 at top.

*Inner petals.*—Outer Surface: Empire Yellow, (HCC) 603, at base, gradually changing through 603/1, to 603/2 to 603/3 at top. Inside Surface: Empire Yellow, (HCC) 603, at base, gradually changing through 603/1, to 603/2 to 603/3 at top.

General color effect of the opened bloom:

*The newly opened flower.*—Chrome Yellow, (HCC) 605/1 through 605/2.

*The 3-days opened flower.*—Empire Yellow, (HCC) 603/3.

Persistence: Petals hang on and dry.

Fragrance: Strong tea.

Lasting quality: About 7 days for cut greenhouse roses kept at living room temperatures.

REPRODUCTIVE ORGANS

Stamens: Many in number regularly arranged about the pistils.

Anthers: Small in size, all opening at once.

*Color.*—Saffron Yellow, (HCC) 7/2.

Filaments: Long, most with anthers.

*Color.*—Begonia, (HCC) 619/1, gradually changing through 619/2, to 619/3 to Saffron Yellow, (HCC) 7/2, at top.

Pollen: Abundant

*Color.*—Egyptian Buff, (HCC) 407/1.

Pistils: Many in number and bunched.

*Styles.*—Uneven, thin and very short.

*Color.*—Pure White, (K) Plate #1.

*Stigmas.*—Color: Delft Rose, (HCC) 020/2.

Ovularies: No seed pods.

Hips: None.

Compared to its seed parent, this new plant is considered to be superior because of its deep rich color and dark glossy foliage which brings out the attractiveness of the variety. Also, it has the advantageous characteristic of a much longer vase life which is seldom found in a yellow rose.

This variety is also much better than its pollen parent, Hoosier Gold, in that it holds a better and more consistent bud shape and color. The color is a richer yellow type floribunda with better growing habits than Hoosier Gold in that it has a longer stretch in stem length and is very productive even in low light conditions.

I claim:

1. A new and distinctive rose plant substantially as herein shown and described, characterized by the rich, deep yellow color of its blooms, enhanced by the glossy green color of its foliage, its vigorous growth habit, and its free and continuous blooming habit.

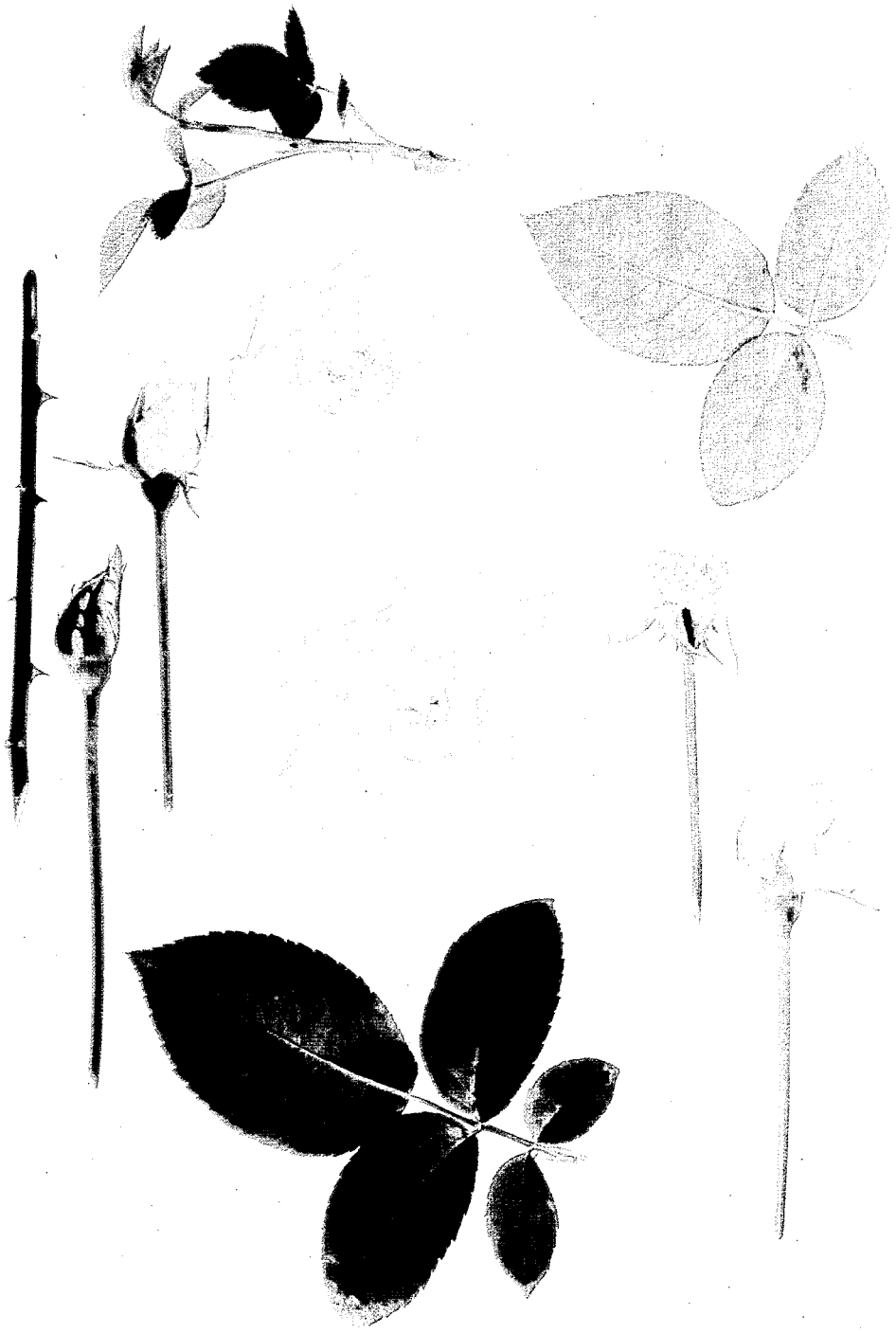

* * * * *